United States Patent [19]

Chadwick et al.

[11] Patent Number: 5,292,909
[45] Date of Patent: Mar. 8, 1994

[54] CATALYTIC CONVERSION OF DIRECT PROCESS HIGH-BOILING COMPONENT TO CHLOROSILANE MONOMERS IN THE PRESENCE OF HYDROGEN CHLORIDE AND HYDROGEN

[75] Inventors: Kirk M. Chadwick, S. Glamorgan, United Kingdom; Ajay K. Dhaul, Carrollton, Ky.; Roland L. Halm, Madison; Richard G. Johnson, Hanover, both of Ind.

[73] Assignee: Dow Corning Corporation, Midland, Mich.

[21] Appl. No.: 91,141

[22] Filed: Jul. 14, 1993

[51] Int. Cl.$^5$ .............................. C07F 7/08
[52] U.S. Cl. ..................... 556/468; 556/466
[58] Field of Search ................. 556/468, 466

[56] References Cited

U.S. PATENT DOCUMENTS

| | | | |
|---|---|---|---|
| 2,380,995 | 8/1945 | Rochow | 556/472 |
| 2,488,487 | 11/1949 | Barry et al. | 556/472 |
| 2,598,435 | 5/1952 | Mohler et al. | 556/468 |
| 2,681,355 | 6/1954 | Barry et al. | 556/468 |
| 2,709,176 | 5/1955 | Bluestein | 556/468 |
| 3,006,943 | 10/1961 | Nitzsche et al. | 556/468 |
| 3,432,537 | 3/1969 | Guinet et al. | 556/468 |
| 3,639,105 | 2/1972 | Atwell et al. | 556/468 |
| 4,059,608 | 3/1977 | Calas et al. | 556/468 |
| 4,079,071 | 3/1978 | Neale | 556/468 |
| 4,461,908 | 7/1984 | Takamizawa et al. | 556/468 X |
| 4,578,495 | 3/1986 | Soula et al. | 556/468 |
| 4,958,040 | 9/1990 | Yoshioka et al. | 556/468 X |
| 5,210,255 | 5/1993 | Kalchauer et al. | 556/468 |

OTHER PUBLICATIONS

Takeda et al., Kogyo Kagaku Zasshi (Journal of Industrial Chemistry), vol. 60, No. 11, pp. 1392-1395 (1957).

*Primary Examiner*—Paul F. Shaver
*Attorney, Agent, or Firm*—Wiliam F. Boley

[57] ABSTRACT

The present invention is a process for converting a high-boiling component resulting from the reaction of an organochloride with silicon into commercially more desirable monosilanes. The process comprises contacting the high-boiling component with hydrogen chloride and hydrogen gas at a temperature within a range of about 250° C. to 1000° C. in the presence of a catalyst selected from a group consisting of activated carbon, alumina, silica, zeolite, AlCl$_3$, AlCl$_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

17 Claims, No Drawings

CATALYTIC CONVERSION OF DIRECT PROCESS HIGH-BOILING COMPONENT TO CHLOROSILANE MONOMERS IN THE PRESENCE OF HYDROGEN CHLORIDE AND HYDROGEN

BACKGROUND OF INVENTION

The present invention is a process for converting a high-boiling component resulting from the reaction of organochloride with silicon into commercially more desirable monosilanes. The process comprises contacting the high-boiling component with hydrogen chloride and hydrogen gas at a temperature within a range of about 250° C. to 1000° C. in the presence of a catalyst selected from a group consisting of activated carbon, alumina, silica, zeolite, AlCl$_3$, AlCl$_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

The high-boiling component useful in the present process results from a process typically referred to as the "Direct Process," where an organohalide is reacted with silicon metalloid in the presence of a suitable catalyst to form monosilanes. The Direct Process as described by, for example, Rochow, U.S. Pat. No. 2,380,995, issued Aug. 7, 1945, and Barry et al., U.S. Pat. No. 2,488,487, issued Nov. 15, 1949. is the main commercial process by which organohalosilanes (i.e. monosilanes), for example, dimethyldichlorosilane and trimethylchlorosilane are formed. These organohalosilanes are reactive compounds which can undergo numerous reactions to form a variety of useful silicon containing compounds and polymers. A major commercial use of organohalosilanes is in the production of polysiloxane polymers which are useful as heat transfer fluids, lubricants, and the like and which can be further processed, for example, to form silicone elastomers, resins, sealants, and adhesives.

Operation of the Direct Process results not only in the production of the desirable monosilanes, but also in a high boiling component typically considered to be all materials with a boiling point higher than the particular diorganodihalosilane produced in the process. The high-boiling component is a complex mixture that includes compounds containing SiSi, SiOSi, SiCSi, SiCCSi, and SiCCCSi linkages in the molecules. Some typical compounds found in a high-boiling component are described, for example, in Mohler et al., U.S. Pat. No. 2,598,435, issued May 27, 1952, and Barry et al., U.S. Pat. No. 2,681,355, issued Jun. 15, 1954. The high-boiling component may also comprise silicon containing solids and soluble and insoluble compounds of copper, aluminum, and zinc.

In current commercial operations for performing the Direct Process, the high-boiling component can constitute as much as ten percent of the resultant product. Therefore, it is desirable to convert the high-boiling component into commercially desirable products to both reduce low value byproducts and to improve raw material utilization.

Mohler, U.S. Pat. No. 2,598,435, issued May 27, 1952, describes a process for converting methylpolysilanes present in a Direct Process residue to monosilanes, the process comprises heating the residue at a temperature above 250° C. and below the decomposition point of the formed monosilanes.

Barry, U.S. Pat. No. 2,681,355, issued Jun. 15, 1954, observed that the process taught in Mohler, U.S. Pat. No. 2,598,435, can result in significant coking of the reactor making the process unsuitable for commercial cracking processes. Barry, supra, teaches that this coking can be reduced if the Direct Process residue is contacted with at least four percent by weight hydrogen chloride at a temperature from 200° C. to 900° C. Barry also suggests that the process can be run in a reactor packed with either an inert material such as quartz or a catalytic material such as activated alumina or silica alumina.

Bluestein, U.S. Pat. No. 2,709,176, issued May 25, 1955, reports a process for converting the polysilanes present in a Direct Process residue into monosilanes by the use of a tertiary organic amine catalyst. Bluestein reports that when the Direct Process residue is contacted with a hydrogen halide and a tertiary organic amine catalyst, the process can be conducted at temperatures of about 75° C. to 150° C. with acceptable yields of monosilanes being obtained.

Atwell et al., U.S. Pat. No. 3,639,105, issued Feb. 1, 1972, describe a process where hydrosilanes are produced by contacting disilane with hydrogen gas under pressure. The resulting mixture is heated in the presence of a transition metal catalyst at temperatures within a range of 25° C. to 250° C. Atwell et al. teach that at temperatures in excess of 250° C catalyst and/or disilane decomposition tends to occur which deleteriously affects the reaction.

Calas et al., U.S. Pat, No. 4,059,608, teach a process for hydrogenating disilanes where a catalyst system containing an aprotic compound and a nickel catalyst is used. Calas et al. teach that the process can be conducted at a temperature within a range of 50° C. to 200° C.

Neale, U.S. Pat. No. 4,079 071, issued Mar. 14, 1978, teaches a process for preparing hydrosilanes by reacting methylchloropolysilanes with hydrogen gas under pressure at a temperature of from about 25° C. to about 350° C. in the presence of a copper catalyst.

Takeda et al., Kogyo Kagaku zasshi (Journal of Industrial Chemistry), Vol. 60, No. 11, p. 1392–1395 (1957), describe the use of alumina, carbon, and pumice as catalyst for the catalytic cracking of disilane in a hydrogen stream.

An objective of the present process is to provide a high yield process for the conversion of a high-boiling component produced by the Direct Process to monosilanes. The present inventors have unexpectedly discovered that the stated objective can be achieved by the catalytic conversion of the Direct Process high-boiling component to chlorosilane monomers in the presence of hydrogen chloride and hydrogen gas. This discovery is even more unexpected in view of the present inventors observation that in the absence of a catalyst, hydrogen chloride and hydrogen gas in combination result in a very poor yield of chlorosilane monomer production.

SUMMARY OF INVENTION

The present invention is a process for converting a high-boiling component resulting from the reaction of an organochloride with silicon into commercially more desirable monosilanes. The process comprises contacting the high-boiling component with hydrogen chloride and hydrogen gas at a temperature within a range of about 250° C. to 1000° C. in the presence of a catalyst selected from a group consisting of activated carbon, alumina, silica, zeolite, $AlCl_3$, $AlCl_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

DESCRIPTION OF INVENTION

The present invention is a process for converting a high-boiling component resulting from the reaction of an organochloride with silicon metalloid (hereafter referred to as silicon) to monosilanes. The process comprises contacting a high-boiling component, resulting from the reaction of an organochloride with silicon, and hydrogen chloride and hydrogen gas at a temperature within a range of about 250° C. to 1000° C. in the presence of a catalyst selected from a group consisting of activated carbon, alumina, silica, zeolite, $AlCl_3$, $AlCl_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

The present process may be run in any standard type reactor for contacting silanes with a catalyst. The process may be run as a batch process, semi-continuous, or continuous process. The process can be run, for example, in a fixed-bed reactor, a stirred-bed reactor, or a fluidized-bed reactor. Preferred is when the process is run as a continuous process in a fluidized-bed reactor.

The present process is useful for converting a high-boiling component resulting from the reaction of an organochloride with silicon to form monosilanes. The term "high-boiling component" refers to those materials with a boiling point above that of the diorganodichlorosilane formed by the reaction of the organochloride with silicon. For example when methyl chloride is reacted with silicon, the diorganodichlorosilane will be dimethyldichlorosilane and the high-boiling component will comprise those materials having a boiling point greater than that of dimethyldichlorosilane, i.e. greater than about 70° C.

In a typical process for reacting an organochloride with silicon, the process is conducted at a temperature of about 270° C. to 350° C., in the presence of a suitable catalyst, and gaseous products and unreacted feed are continuously removed from the process. The removed gaseous products and unreacted feed are subsequently distilled to remove monosilanes leaving a high-boiling component.

The high-boiling component is a complex mixture that can include compounds containing SiSi, SiOSi, SiCSi, SiCCSi, and SiCCCSi linkages alone or in combination in each molecule. The high-boiling component can include silicon containing solids and soluble and insoluble compounds of copper, aluminum, and zinc. The high-boiling component may contain, for example, organic substituted and non-organic substituted silanes, disilanes, trisilanes, disiloxanes, silane oligomers, siloxane oligomers, silalkylenes, and silicon containing solids, all of which may be converted to monosilanes by the present process.

The present process is useful for converting polysilanes in the high-boiling component to monosilanes, where the polysilanes are described by formula $R_aH_b$-$Si_nCl_{2n+2-a-b}$ and where each R is a radical independently selected from a group consisting of alkyls comprising one to six carbon, n=2 to 20, a=0 to 2n+2, b=0 to 2n+2, and a+b=0 to 2n+2.

The polysilanes useful in the present process can consist of n number of silicon atoms where n is an integer from two to 20. Preferred is when n equals two. The polysilanes can be substituted with a=0 to 2n+2 number of R radicals, where each R is independently selected from a group consisting of alkyls of one to six carbon atoms. The radical R can be, for example, methyl, ethyl, propyl, and t-butyl. Preferred is when R is methyl.

The polysilanes in the high-boiling component can contain b number of hydrogen atoms substituted on the silicon atoms. where b=0 to 2n+2.

The polysilanes in the high-boiling component can contain from zero to 2n+2 chlorine atoms.

The high-boiling component can contain silalkylenes, where each silalkylene molecule can comprise one or more silalkylene bonds described by formula $Si(C)_zSi$ and z is an integer from one to six. Preferred is when z is an integer from one to three. The silalkylene molecules can comprise SiSi bonds and SiOSi bonds as well as the silalkylene bonds. The silicon atoms of the silalkylene molecules can be further substituted with the radical R, where R is as previously described, with chlorine, and with hydrogen. Preferred is when the silicon atoms of the silalkylenes are substituted with methyl.

The preferred high-boiling component is one resulting from the reaction of methyl chloride with silicon, the high boiling component having a boiling point greater than about 70° C. This high-boiling component can contain, for example, $Me_2ClSiSiMe_2Cl$, $Me_2ClSiSiMeCl_2$, $MeCl_2SiSiMeCl_2$, $Me_2ClSiSi(Me)(Cl)SiMeCl_2$, $Me_2ClSiCH_2SiMe_2Cl$, $Me_2ClSiCH_2SiMeCl_2$, $MeCl_2SiCH_2SiMeCl_2$, $Me_2ClSi(CH_2)_2SiMeCl_2$, $Me_2ClSi(CH_2)_3SiMeCl_2$, $Me_2ClSiCH_2Si(Me)(Cl)SiMeCl_2$, $Me_2ClSiCH_2Si(Me)(Cl)CH_2SiMeCl_2$, and $Me_2ClSiOSiMeCl_2$, where Me is methyl, all of which may be converted to monosilanes by the present process.

The high-boiling component is contacted with hydrogen chloride and hydrogen gas, where the ratio of the weight of high-boiling component added to the reactor to the weight of hydrogen chloride added to the reactor is within a range of about 5:1 to 0.05:1. Preferred is where the ratio of the weight of high-boiling component to the weight of hydrogen chloride is within a range of about 3:1 to 1:1.

The high-boiling component is contacted with hydrogen chloride and hydrogen gas, where the ratio of the weight of high-boiling component added to the reactor to the weight of hydrogen gas added to the reactor is within a range of about 0.1:1 to 1000:1. Preferred is where the ratio of the weight of high-boiling component to the weight of hydrogen gas is within a range of about 1:1 to 500:1.

The process is conducted at a temperature within a range of about 250° C. to 1000° C. A preferred temperature is within a range of about 270° C. to 650° C.

While pressure is not critical to the present process, it is preferred that the process be run at a pressure within a range of about 20 psig to 1000 psig.

The process is conducted in the presence of a catalyst selected from a group consisting of activated carbon, alumina, silica, zeolite, $AlCl_3$, $AlCl_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

The physical form of the catalyst is not critical to the present invention and can be, for example, powder, particles, flakes, chips, and pellets.

A preferred catalyst is activated carbon. By "activated carbon" it is meant a microcrystalline, nongraphite form of carbon, having an internal porosity, the carbon having been activated by any standard process known in the art for producing activated carbon, for example, chemical activation or gas activation as described in Kirk-Othmer, Concise Encyclopedia of Chemical Technology, John Wiley & Sons publishers, 1985, p. 204 to 205.

In general, it is preferred that the activated carbon have a diameter within a range of about 0.001 mm to 20 mm. More preferred is when the activated carbon has a diameter within a range of about 0.01 mm to 5 mm and a surface area greater than about 1000 m$^2$/g.

The catalyst can be alumina, i.e. $Al_2O_3$. The size of the alumina is not critical to the present process and is generally determined by availability and the ability to handle. Generally alumina with a particle size within a range of about 0.001 mm to 10 mm is considered useful.

The catalyst can be silica. The silica can be, for example, precipitated silica or fumed silica. Generally silica with a particle size within a range of about 0.001 to 10 mm is considered useful.

The catalyst can be a zeolite. The zeolite catalyst can be of the natural occurring type, for example, chabazite, mordenite, erionite, faujasite, and clinoptilolite. The zeolite catalyst can be a synthetic zeolite, for example, of the zeolite A, X, L, or Y types or of the high silica synthetic zeolite types such as ZSM-5 and ZSM-11. Preferred is when the zeolite catalyst is selected from a group of synthetic zeolite catalysts consisting of LZ-Y-64, LZ-Y-74, and LZ-M-8.

The weight of activated carbon, alumina, silica, or zeolite catalyst added to the process in relation to the weight of high-boiling component, hydrogen chloride, and hydrogen added to the process will depend upon such factors as the type of catalyst, chemical composition of the high-boiling component, process temperature, type of reactor employed, and desired conversion and product selectivity. When the process is run as a batch process or a semi-continuous process a useful weight of catalyst is considered to be within a range of about 0.1 to 30 weight percent of the combined weight of the high-boiling component, hydrogen chloride, and hydrogen gas added to the process.

The catalyst can be $AlCl_3$. The concentration of $AlCl_3$ used in the process will depend upon such factors as discussed for the use of activated carbon. In general, when the process is run as a batch process or semi-continuous process a useful concentration of $AlCl_3$ catalyst is considered to be within a range of about 0.1 to 30 weight percent of the combined weight of the high-boiling component, the hydrogen chloride, and the hydrogen added to the process.

The catalyst can be $AlCl_3$ supported on a support selected from a group consisting of carbon, silica, and alumina. The amount of $AlCl_3$ supported on the support can be from about 0.1 to 20 weight percent $AlCl_3$. Preferred is when the amount of $AlCl_3$ supported on the support is within a range of about 0.5 to 5.0 weight percent $AlCl_3$. The concentration of supported $AlCl_3$ used in the process will depend upon such factors as discussed for the use of activated carbon. In general, when the process is run as a batch process or semi-continuous process a useful concentration of supported $AlCl_3$ catalyst is considered to be that which provides a concentration of $AlCl_3$ within a range of about 0.1 to 30 weight percent of the combined weight of the high-boiling components, the hydrogen chloride, and the hydrogen added to the process.

The catalyst can be platinum supported on a support selected from a group consisting of carbon, silica, and alumina or palladium supported on a support selected from a group consisting of carbon, silica, and alumina. The amount of platinum or palladium supported on the support can be from about 0.1 to 10 weight percent. Preferred is when the amount of platinum or palladium supported on the support is within a range of about 0.5 to 2.0 weight percent. The concentration of supported platinum or supported palladium used in the process will depend upon such factors as discussed for the use of activated carbon.

The optimum contact time for the high-boiling component, hydrogen, and hydrogen chloride with the catalyst will depend, for example, on factors such as the type of catalyst, chemical composition of the high-boiling component, and the degree of conversion and product selectivity desired. In general a contact time within a range of about one second to five hours is considered useful. Longer contact times may be employed, but appear to offer no advantage and may result in excessive scission of silicon-carbon bonds and silicon-hydrogen bonds present in the monosilanes.

If desired, the monosilane containing product of the present process can be further separated by standard means, for example, distillation to separate the monosilanes from a high-boiling component and the high-boiling component recycled to the process.

The following examples are provided to facilitate understanding and to demonstrate the effectiveness of the present invention. These examples are not intended to limit the scope of the claims provided herein.

EXAMPLE 1

(Not within the scope of the present invention). A high-boiling component resulting from the reaction of methyl chloride with silicon was contacted with hydrogen chloride in the absence of catalyst. The reactor consisted of a 2.5 cm diameter by 50 cm length quartz tube maintained at about 500° C. The high-boiling component comprised by weight, 55% methylchlorodisilane, 5% disilmethylenes, 35% other polysilanes and silalkylenes, and 5% silicon containing solids. The high-boiling component was fed at a rate of 117 g/h to the reactor and hydrogen chloride was fed to the reactor at 50 g/h. The process was conducted for one hour with gaseous product exiting the reactor being collected in a cold condenser. The condensed product was analyzed by gas chromatography using a thermal conductivity detector (GC-TC). Chlorosilane monomers detected included $HSiCl_3$, $SiCl_4$, $MeHSiCl_2$, $Me_3SiCl$, $MeSiCl_3$, and $Me_2SiCl_2$. The condensed product also contained methylchlorodisilanes, disilmethylenes, and other polysilanes and silalkylenes. The chlorosilane monomer yield of the process was calculated as the gram moles of monomer in the product divided by the gram moles of silicon fed to the process the quotient multiplied by 100. The chlorosilane monomer yield for this Example was 48 percent.

EXAMPLE 2

(Not within the scope of the present invention) A high-boiling component resulting from the reaction of methyl chloride with silicon was contacted with hydrogen chloride in the presence of a packed bed of activated carbon catalyst. The process was conducted similar to that described in Example 1, with the high-boiling component composition, reactor design, and reaction temperature being the same. The reactor was packed with 12 g of Calgon BPL 1 mm by 3.3 mm activated carbon pellets (Calgon, Pittsburgh. Pa.). The high-boiling component was fed to the reactor at a rate of 92 g/h and hydrogen chloride was fed to the reactor at a rate of 57 g/h. Gaseous product exiting the reactor was collected and analyzed as described in Example 1. The chlorosilane monomer yield was 79 percent.

EXAMPLE 3.

(Not within the scope of the present invention) A high-boiling component resulting from the reaction of methyl chloride with silicon was contacted with hydrogen gas in the presence of a packed bed of activated carbon catalyst. The process was conducted similar to that described in Example 1, with the high-boiling component composition, reactor design, and reaction temperature being the same. The reactor was packed with 17 g of Calgon BPL 1 mm by 3.3 mm activated carbon pellets (Calgon, Pittsburgh, Pa.). The high-boiling component was fed to the reactor at a rate of 101 g/h and hydrogen gas was fed to the reactor at a rate of 3 g/h. Gaseous product exiting the reactor was collected and analyzed as described in Example 1. The chlorosilane monomer yield was 29 percent.

EXAMPLE 4

(Not within the scope of the present invention) A high-boiling component resulting from the reaction of methyl chloride with silicon was contacted with hydrogen chloride and hydrogen gas. The process was conducted similar to that described in Example 1, with the high-boiling component composition, reactor design, and reaction temperature being the same. The high-boiling component was fed to the reactor at a rate of 94 g/h, hydrogen chloride was fed to the reactor at a rate of 60 g/h and hydrogen gas was fed to the reactor at a rate of 0.1 g/h. The process was conducted for one hour with gaseous product exiting the reactor being collected and analyzed as described in Example 1. The chlorosilane monomer yield was 21 percent.

EXAMPLE 5

A high-boiling component resulting from the reaction of methyl chloride with silicon was contacted with hydrogen chloride and hydrogen gas in the presence of a packed bed of activated carbon catalyst. The process was conducted similar to that described in Example 1, with the high-boiling component, reactor design, and reaction temperature being the same. The reactor was packed with 16 g of Calgon BPL 1 mm by 3.3 mm activated carbon pellets (Calgon, Pittsburgh, Pa.). The high-boiling component was fed to the reactor at a rate of 66 g/h, hydrogen chloride was fed to the reactor at a rate of 61 g/h, and hydrogen gas was fed to the reactor at a rate of 0.4 g/h. The process was conducted for one hour with gaseous product exiting the reactor being collected and then analyzed as described in Example 1. The chlorosilane monomer yield was 84 percent.

We claim:

1. A process for converting a high-boiling component resulting from the reaction of an organochloride with silicon, to monosilanes, the process comprising: contacting a high-boiling component, resulting from the reaction of an organochloride with silicon, and hydrogen chloride and hydrogen gas at a temperature within a range of about 250° C. to 1000° C. in the presence of a catalyst selected from a group consisting of activated carbon, alumina, silica, zeolite, $AlCl_3$, $AlCl_3$ supported on a support selected from a group consisting of carbon, silica, and alumina; platinum supported on a support selected from a group consisting of carbon, silica, and alumina; and palladium supported on a support selected from a group consisting of carbon, silica, and alumina.

2. A process according to claim 1, where the temperature is within a range of about 270° C. to 650° C.

3. A process according to claim 1, where the high-boiling component, the hydrogen chloride, and the hydrogen gas are contacted at a pressure within a range of about 20 psig to 1,000 psig.

4. A process according to claim 1, where the ratio of the weight of high-boiling component added to the reactor to the weight of hydrogen chloride added to the reactor is within a range of about 5:1 to 0.05:1.

5. A process according to claim 1, where the ratio of the weight of high-boiling component added to the reactor to the weight of hydrogen chloride added to the reactor is within a range of about 3:1 to 1:1.

6. A process according to claim 1, where the ratio of the weight of high-boiling component added to the reactor to the weight of hydrogen added to the reactor is within a range of about 0.1:1 to 1000:1.

7. A process according to claim 1, where the ratio of the weight of high-boiling component added to the reactor to the weight of hydrogen added to the reactor is within a range of about 1:1 to 500:1.

8. A process according to claim 1, where the high-boiling component results from the reaction of methyl chloride with silicon.

9. A process according to claim 1, where the high-boiling component comprises polysilanes and silalkylenes.

10. A process according to claim 1, where the high-boiling component comprises polysilanes described by formula $R_aH_bSi_nCl_{2n+2-a-b}$, where each R is a radical independently selected from a group consisting of alkyls comprising one to six carbon atoms, $n=2$ to 20, $a=0$ to $2n+2$, $b=0$ to $2n+2$, and $a+b=0$ to $2n+2$.

11. A process according to claim 10, where R is methyl.

12. A process according to claim 1, where the high-boiling component comprises silalkylenes comprising one or more silalkylene bonds described by formula $Si(C)_zSi$ and $z=1, 2,$ or $3$.

13. A process according to claim 1, where the high-boiling component comprises soluble and insoluble compounds of copper, aluminum, and zinc.

14. A process according to claim 1, where the catalyst is activated carbon.

15. A process according to claim 14, where the activated carbon has a diameter within a range of about 0.01 mm to 5 mm.

16. A process according to claim 1, where the high-boiling component results from the reaction of methyl chloride with silicon and the high-boiling component comprises polysilanes, silalkylenes, silicon containing solids, and soluble and insoluble compounds of copper, aluminum, and zinc.

17. A process according to claim 16, where the catalyst is activated carbon having a diameter within a range of about 0.01 mm to 5 mm and a surface area greater than about 1000 $m^2/g$.

* * * * *